(12) United States Patent
Raval

(10) Patent No.: US 11,707,563 B2
(45) Date of Patent: Jul. 25, 2023

(54) ADVANCED DIALYSIS CATHETER WITH PRESSURE SENSOR

(71) Applicant: ADVENTIST HEALTH SYSTEM/SUNBELT, INC., Altamonte Springs, FL (US)

(72) Inventor: Nirav Raval, Orlando, FL (US)

(73) Assignee: ADVENTIST HEALTH SYSTEM/SUNBELT, INC., Altamonte Springs, FL (US)

( * ) Notice: Subject to any disclaimer, the term of this patent is extended or adjusted under 35 U.S.C. 154(b) by 5 days.

(21) Appl. No.: 17/012,963

(22) Filed: Sep. 4, 2020

(65) Prior Publication Data

US 2021/0069404 A1     Mar. 11, 2021

Related U.S. Application Data

(60) Provisional application No. 62/897,029, filed on Sep. 6, 2019.

(51) Int. Cl.
*A61M 1/36* (2006.01)
*A61M 25/01* (2006.01)
*A61M 25/00* (2006.01)

(52) U.S. Cl.
CPC ........ *A61M 1/3656* (2014.02); *A61M 25/003* (2013.01); *A61M 25/0108* (2013.01); *A61M 2025/0031* (2013.01); *A61M 2205/0244* (2013.01); *A61M 2205/3344* (2013.01); *A61M 2205/50* (2013.01); *A61M 2230/30* (2013.01); *A61M 2230/50* (2013.01)

(58) Field of Classification Search
CPC .................. A61M 1/36; A61M 1/3661; A61M 2025/0031
See application file for complete search history.

(56) References Cited

U.S. PATENT DOCUMENTS

| 4,718,423 A | 1/1988 | Willis et al. |
| 4,947,852 A * | 8/1990 | Nassi ........................ A61B 8/06 600/469 |
| 5,048,532 A | 9/1991 | Hickey |
| 5,078,148 A | 1/1992 | Nassi et al. |

(Continued)

FOREIGN PATENT DOCUMENTS

| WO | 2013/159072 A1 | 10/2013 |
| WO | 2014/168737 A1 | 10/2014 |
| WO | 2018/170364 A1 | 9/2018 |

OTHER PUBLICATIONS

Postdialysis Hypertension: Associated Factors, Patient Profiles, and Cardiovascular Mortality. Attilio Losito et al, American Journal of Hypertension, 29(6), Jun. 2016, pp. 684-689. (Year: 2016).*

(Continued)

*Primary Examiner* — Laura A Bouchelle
(74) *Attorney, Agent, or Firm* — McCarter & English, LLP

(57) ABSTRACT

The present disclosure relates to a hemodialysis catheter that can monitor intravascular pressure using a MEMS sensor. The hemodialysis catheter comprises a venous lumen, an atrial lumen, and at least one MEMS system sensor. The hemodialysis catheter also comprises a data acquisition and processing system. The hemodialysis catheter can communicate with a monitor system to display pressure data.

9 Claims, 3 Drawing Sheets

(56) References Cited

U.S. PATENT DOCUMENTS

| | | | | |
|---|---|---|---|---|
| 6,162,182 | A * | 12/2000 | Cole | A61B 5/0215 600/488 |
| 7,909,770 | B2 | 3/2011 | Stern et al. | |
| 7,988,658 | B2 * | 8/2011 | Quinn | A61M 1/3659 604/266 |
| 9,532,724 | B2 * | 1/2017 | Grunwald | A61B 5/352 |
| 2005/0197585 | A1 | 9/2005 | Brockway et al. | |
| 2008/0154186 | A1 * | 6/2008 | Appling | A61M 25/0068 604/43 |
| 2009/0024015 | A1 | 1/2009 | Curry | |
| 2009/0101577 | A1 * | 4/2009 | Fulkerson | B01D 61/22 600/485 |
| 2010/0234698 | A1 * | 9/2010 | Manstrom | A61B 5/0017 600/478 |
| 2011/0282217 | A1 | 11/2011 | Nashef | |
| 2012/0172731 | A1 | 7/2012 | Smith | |
| 2013/0274619 | A1 | 10/2013 | Stone et al. | |
| 2013/0303962 | A1 * | 11/2013 | Bernard | A61M 1/365 366/144 |
| 2015/0057532 | A1 | 2/2015 | Belleville | |
| 2015/0351645 | A1 | 12/2015 | Hiltner | |
| 2016/0287278 | A1 | 10/2016 | Stigall et al. | |
| 2017/0027458 | A1 | 2/2017 | Glover et al. | |
| 2018/0010974 | A1 | 1/2018 | Bueche et al. | |
| 2018/0263515 | A1 | 9/2018 | Raval | |
| 2021/0236802 | A1 * | 8/2021 | Buckley | A61M 60/38 |

OTHER PUBLICATIONS

Hocht, Blood Pressure Variability: Prognostic Value and Therapeutic Implications, ISRN Hypertension, vol. 213, Article ID 398485). (Year: 2013).*

U.S. Appl. No. 16/825,309, filed Mar. 20, 2020, Pending.

Brancato et al., An Implantable Intravascular Pressure Sensor for a Ventricular Assist Device. Micromachines (Basel). Aug. 8, 2016;7(8):135, 17 pages.

International Search Report and Written Opinion for Application No. PCT/US2018/022807, dated Jun. 1, 2018, 14 pages.

International Search Report for Application No. PCT/US2020/049426, dated Nov. 25, 2020, 5 pages.

* cited by examiner

ADVANCED DIALYSIS CATHETER WITH PRESSURE SENSOR

This application claims priority under 35 USC § 119 to U.S. Provisional Application No. 62/897,029, which was filed on Sep. 6, 2019 and is herein incorporated by reference in its entirety.

The present disclosure relates generally to hemodialysis catheters with at least one microelectricalmechanical system (MEMS) sensor.

Hemodialysis is a treatment for kidney disease involving pumping a patient's blood through a dialysis machine to filter excess solutes and toxins from the blood. Some patients receive hemodialysis through arteriovenous fistulas. However, these fistulas can take months to mature and be ready for use. Certain hemodialysis patient groups require immediate vascular access or continuous renal replacement therapy, both of which can be achieved with long-dwelling hemodialysis catheters.

With long-dwelling, vascular catheters, there is a risk of lumen occlusion, which can prevent blood flow in the catheter, or the formation of a fibrin sheath, which can occlude blood flow in the host blood vessel. Monitoring of pressure in and around hemodialysis catheters can lead to early detection of either of these occlusions.

Therefore, there is a need for improved hemodialysis catheters that overcome some of the drawbacks of currently available devices. Accordingly, the present disclosure relates to hemodialysis catheters with MEMS sensors and a monitoring system for use in conjunction with such catheters, which provide advantages over existing devices.

SUMMARY

The present disclosure relates generally to hemodialysis catheters with improved diagnostics and treatment capabilities. The hemodialysis catheter may comprise an elongate member having a proximal end, a distal end, a first tubular component and a second tubular component. In some embodiments, the first tubular component and second tubular component extend from the proximal end to the distal end of the elongate member. In certain embodiments, the second tubular member extends a further distance from the proximal end of the elongate member than does the first tubular component.

The hemodialysis catheter includes at least one MEMS sensor disposed proximate a distal end of the second tubular component. The hemodialysis catheter also includes a connector hub at the proximal end of the elongate member and at least one access line affixed to the connector hub in communication with at least a portion of the elongate member. In certain embodiments, the first and second tubular components of the hemodialysis catheter comprise two halves of a single extrusion. Further, the first tubular component includes at least one lumen for blood flow out of the patient. Also, the second tubular member comprises at least a first lumen and a second lumen, wherein the first lumen is designated for blood returning to the patient and the second lumen is designated for the microelectricalmechanical system sensor.

In another embodiment, the present disclosure provides methods of performing hemodialysis comprising inserting a portion of a hemodialysis catheter of the present disclosure into the vasculature of a patient. The hemodialysis catheter includes a venous lumen, an atrial lumen, and at least one MEMS sensor near a distal end of the hemodialysis catheter. The methods of performing hemodialysis further comprise zeroing the microelectricalmechanical system sensor and analyzing the microelectricalmechanical system sensor waveform to determine a position of the catheter relative to the heart. Next, the methods include initiating blood flow from the patient, through the atrial lumen, to a dialyzer, through the venous lumen, and into the vasculature of the patient. Further, the methods include measuring central venous pressure and assessing volume status. Once sufficient hemodialysis is performed, the method next includes stopping the blood flow from the patient and assessing closing pressure post-treatment.

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

DETAILED DESCRIPTION OF EXEMPLARY EMBODIMENTS

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including" as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Embodiments of the present disclosure relate to hemodialysis catheters with at least one microelectricalmechanical system (MEMS) sensor. Hemodialysis catheters of the present disclosure acquire various physiologic measurements related to vascular health and conditions of the catheter lumen. The present disclosure also provides a system to receive, record, transmit, and/or display pertinent data. The hemodialysis catheter is equipped at least one sensor, including, but not limited to, a MEMS pressure sensor.

Figure 1:
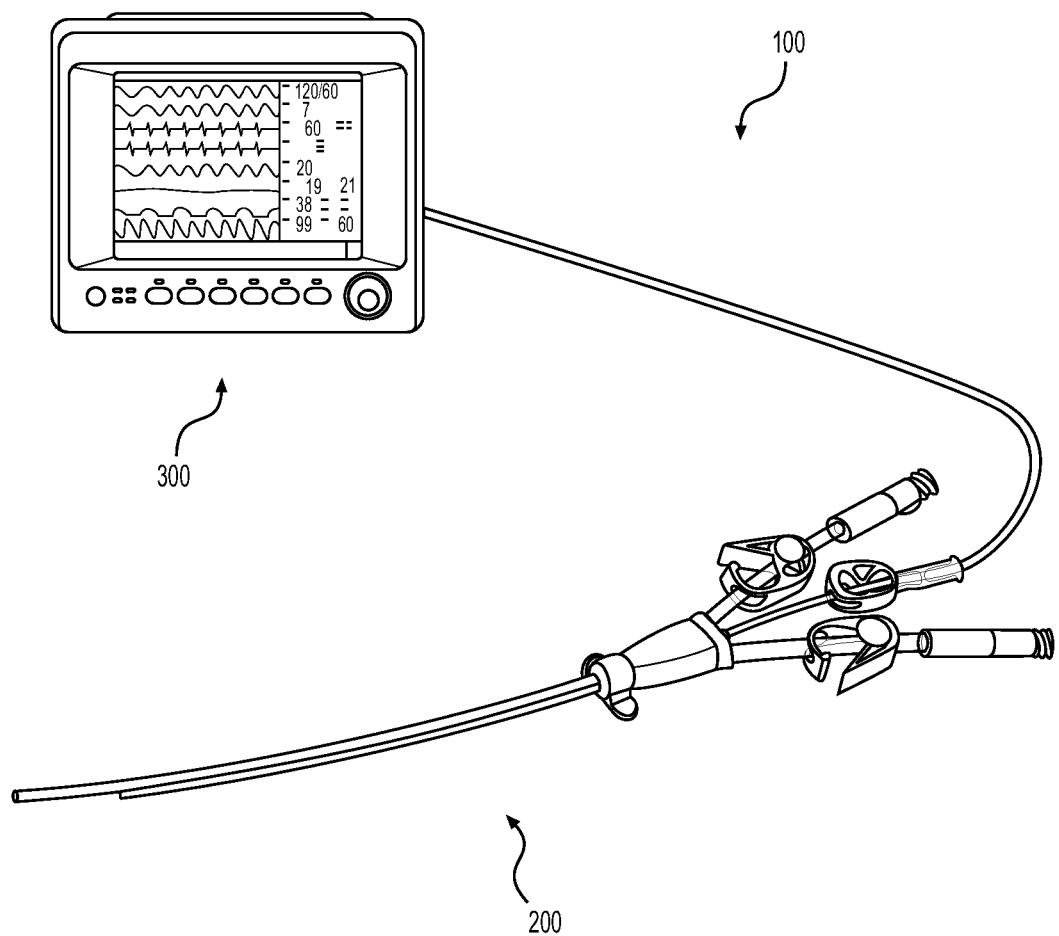
FIG. 1 illustrates a hemodialysis catheter and monitoring system, according to various embodiments

An embodiment of an exemplary hemodialysis catheter and monitoring system is shown in FIG. 1. As shown in FIG. 1, system 100 can include hemodialysis catheter 200 and monitoring system 300, as well as the various components of the hemodialysis catheter and monitoring system.

Figure 2:
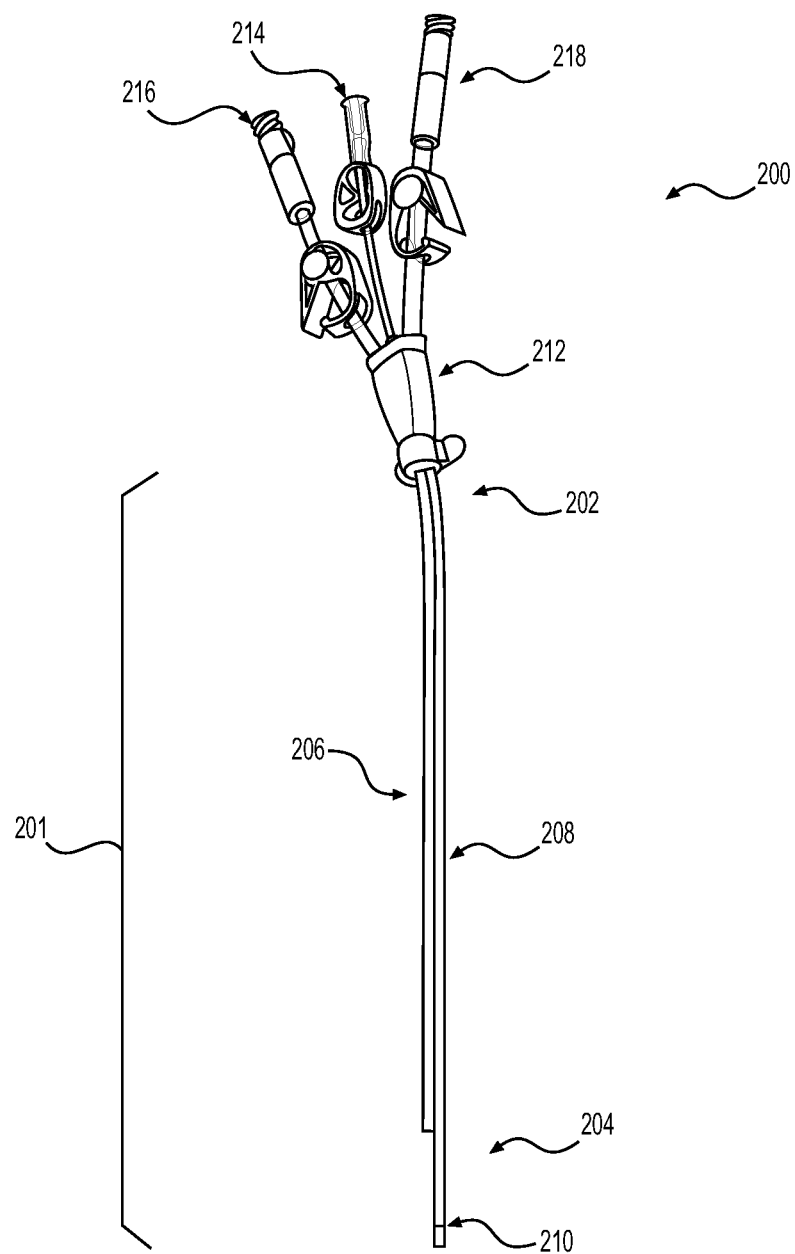
FIG. 2 illustrates one embodiment of a hemodialysis catheter such as the hemodialysis catheter shown in FIG. 1.

FIG. 2 illustrates an exemplary hemodialysis catheter 200. In some embodiments, hemodialysis catheter 200 comprises elongate member 201 having proximal end 202 and distal end 204. In various embodiments, elongate member 201 comprises a flexible material. In some embodiments, elongate member 201 comprises a biocompatible polymer, elastomer, silicon, nylon, combinations of desirable materials, or any suitable biocompatible material. In various embodiments, elongate member 201 comprises at least one of polyurethane, polyethylene, polyvinylchloride, polytetrafluoroethylene, or nylon.

The materials of elongate member 201 can be selected to produce desired mechanical, biologic, and/or chemical properties. For example, the materials can be selected to allow a desired stiffness/flexibility, to prevent undesired chemical reaction with physiologic fluids, or to resist or prevent infection, thrombus formation, or other adverse clinical consequences. According to various embodiments, the surfaces of elongate member 201 are coated with a hydrophilic coating to reduce friction with various organs and tissues while the catheter is manipulated within the patient. In some embodiments, elongate member 201 can comprise a heparin-based or other anti-thrombotic coating to prevent blood clotting in and around the device during use.

In various embodiments, elongate member 201 is provided in a variety of sizes and configurations to aptly suit a variety of patient sizes and anatomies. For example, the length of elongate member 201 can measure about 10, 12, 14, 16, 18, 20, 22, 24, 26, 28, 30, 35, 40, or 50 cm. These values may be used to define lengths of elongate member 201, such as 14 cm, or ranges of lengths, such as 18-20 cm or 14-20 cm.

Additionally, elongate member 201 can be provided in a variety of diameters, defined in medicine using the French (Fr) scale, which provides catheter diameter in values equaling three times the diameter, in millimeters, thereof. In some embodiments, elongate member 201 is provided in 9.5, 10, 10.5, 11, 11.5, 12, 12.5, 13, 13.5, or 14 Fr. These values may be used to define discrete diameters of elongate member 201, such as 11.5 Fr or 12.5 Fr. The diameter of elongate member 201 will allow for adequate hemodialysis blood flow rates and accommodate various quantities and sizes of lumens to be extruded therein.

According to various embodiments, elongate member 201 further comprises first tubular component 206 and second tubular component 208. In some embodiments, first tubular component 206 and second tubular component 208 extend from proximal end 202 to distal end 204 of elongate member 201. As shown in FIG. 2, in various embodiments, second tubular component 208 extends a further distance from proximal end 202 of elongate member 201 than does first tubular component 206. Staggering the terminal ends of first tubular component 206 and second tubular component 208 protects against recirculation of blood during hemodialysis.

Figure 3:
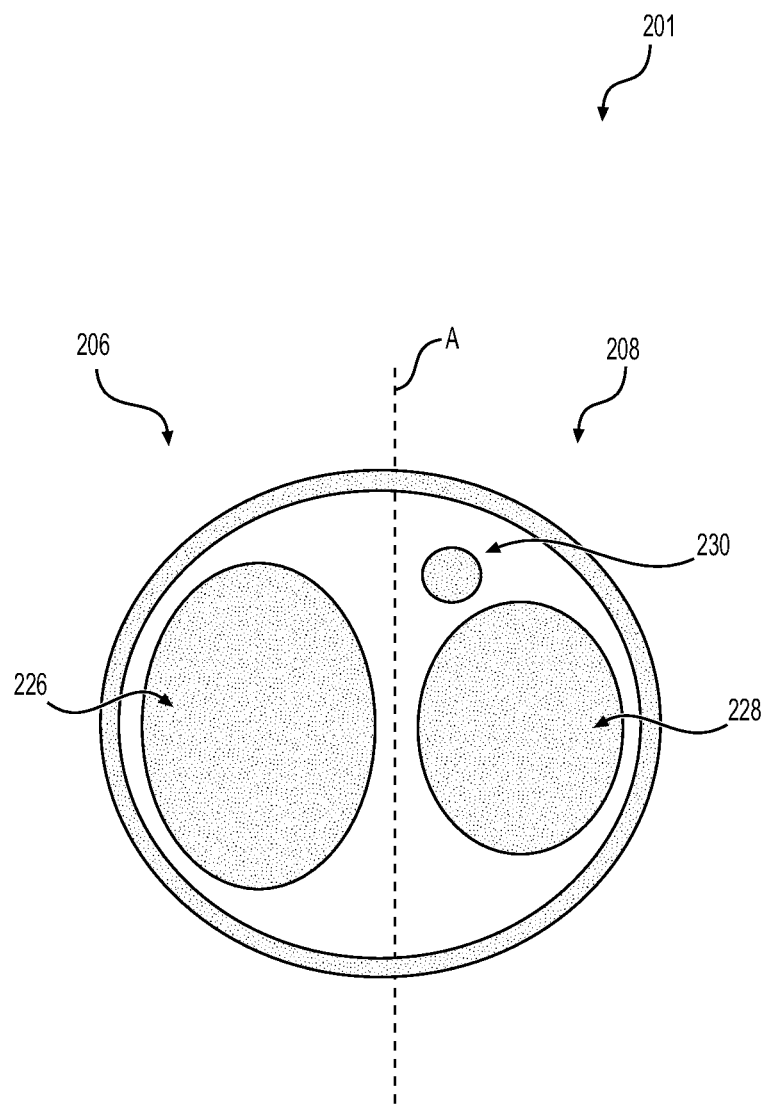
FIG. 3 illustrates one embodiment of a hemodialysis catheter cross-section provided in accordance with the present disclosure.

FIG. 3 illustrates one embodiment of a hemodialysis catheter cross-section provided in accordance with the present disclosure. According to various embodiments, first tubular component 206 and second tubular component 208 comprise two approximate halves of a single extrusion. As shown in FIG. 3, the single extrusion is elongate member 201 and line A separates first tubular component 206 from second tubular component 208. In other embodiments, the cross-section of elongate member 201 may be provided in a figure-eight configuration. Various cross-sections and configurations of elongate member 201 are contemplated in the present disclosure.

In various embodiment, first tubular component 206 comprises at least one lumen 226 for blood flowing out of the patient. In some embodiments, blood flowing through lumen 226 is venous blood to be processed through a dialyzer. In some embodiments, second tubular member 208 comprises first lumen 228 and second lumen 230. In some embodiments, first lumen 228 is designated for blood that has been processed by the hemodialysis machine to return to the patient. In some embodiments, second lumen 230 is designated to store the MEMS sensor and/or the optional wiring required to power the sensor and transmit data to monitor system 300. In some embodiments, lumen 226 and first lumen 228 comprise an ovoid shape. In other embodiments, second tubular member 208 comprises additional lumen 230, which can be used to house more sensors or for administering medicine into the blood stream of the patient.

Returning to FIG. 2, according to various embodiments hemodialysis catheter 200 further comprises connector hub 212 at proximal end 202 of elongate member 201. In some embodiments, connector hub 212 comprises at least one of a y-connector or a manifold connector. Connector hub 212 connects lumen 226, 228, and 230 within elongate member 209, and as displayed in FIG. 3, to access lines 216, 218, and 214 affixed to connector hub 212. In various embodiments, access lines of hemodialysis catheter 200 allow users to perform various functions through the catheter from outside of the body.

In various embodiments, hemodialysis catheter 200 may comprise multiple access lines. For example, hemodialysis catheter 200 may comprise two, three, four, five, six, seven or eight access lines. In some embodiments, access lines may be distinctly marked or colored to enable users to easily distinguish one access line from another. For example, access lines can be color coded.

As shown in FIG. 2, access line 216 is color coded with blue pieces. In various embodiments, access line 216 is connected to first tubular component 206 and is connected to input blood into a hemodialysis machine. In various embodiments, access line 218 is color coded with red pieces and connects to first tubular component 206. Access line 218 may also connect to the output of a hemodialysis machine to facilitate the return of processed blood into the vasculature of the patient.

In some embodiments, additional access line 214 is used to connect the wire of the MEMS sensor in second lumen 230 with the monitoring system to provide pressure data from distal end 204 of elongate member 201.

In some embodiments, access lines 216, 214, and 218 of the disclosed device may comprise single-lumen or multi-lumen tubing. In various embodiments, access lines 216, 214, and 218 can bifurcate into two additional access lines.

In some embodiments, access lines 216, 214, and 218 are affixed with connectors at the proximal ends thereof, such that additional devices may be attached to the access line. In some embodiments, the disclosed connectors comprise at least one of a mechanical connector, luer connector, barb connector, electronic connector, usb-type connector, or pin connector. For example, access line 216 can comprise a luer connector at its proximal end to enable to the hemodialysis machine. In further example, MEMS wiring and power line terminates in a pressure-fit, non-locking plug at access line 214. In this configuration, a reusable wire with conductive ends for both power and data can be used with the MEMS sensor.

In some embodiments, elongate member 201 comprises additional lumens to provide vascular access, drug delivery, sensor containment, access for additional catheters, and physiologic monitoring. To provide fluid communication or access to the vasculature of a patient hemodialysis catheter 200 comprises at least one opening extending between at least one lumen and the exterior of hemodialysis catheter 200.

In some embodiments, elongate member 201 contains openings of various sizes in various locations along the length of the catheter body. Openings can be voids in elongate member 201 through which fluid in the lumen can flow into or out of the catheter. In some embodiments, there are openings at the distal ends of first tubular component 206 and second tubular component 208 to enable patient blood to enter and exit elongate member 201.

In various embodiments, the openings at the distal ends of first tubular component 206 and second tubular component 208 are shaped to increase laminar flow in hemodialysis catheter 200. In some embodiments, the increase in laminar flow reduces the disruption or damage of cellular elements in blood, which, in turn, reduces hemolysis, platelet activation, white blood cell damage.

An important function of hemodialysis catheter 200 is to provide physiological monitoring. In various embodiments, hemodialysis catheter 200 may contain at least one MEMS sensor 210 disposed proximate the distal end of second tubular component 208. In various embodiments, MEMS sensor 210 is a pressure sensor. MEMS pressure sensor 210 may be positioned within lumen 230 or near an outer surface of second tubular component 208. In some embodiments, MEMS sensor 210 is positioned on an outer surface of hemodialysis catheter 200. In some embodiments, MEMS sensor 210 can be coated with an electrically insulating material and covered with an electrically insulating material after attachment to hemodialysis catheter 200, e.g., to comply with federal safety regulations. In various embodiments, MEMS sensor 210 is mounted on or in hemodialysis catheter 200 such that it does not impede blood flow. Such a configuration of sensor 210 reduces the likelihood of thrombosis or the development of a fibrin coating on hemodialysis catheter 200.

In some embodiments, hemodialysis catheter 200 can incorporate visualization components, such as radiopaque markers. Such markers can allow clinicians to appropriately position determine hemodialysis catheter 200 within the patient during, for example by using fluoroscopy or other imaging methods. In various embodiments, a radiopaque marker is placed at the locations of MEMS sensor 210 to allow precise positioning of hemodialysis catheter 200 within the vasculature of the patient.

In some embodiments, hemodialysis catheter 200 further comprises at least one temperature sensor, such as a MEMS temperature sensor. MEMS temperature sensors can measure temperatures to assist during the monitoring of fever and anesthesia-induced thermoregulatory complications. In various embodiments, MEMS temperature sensors provides continuous, absolute temperature measurements, and aid medical professionals in performing diagnostic procedures.

In some embodiments, the distal end of hemodialysis catheter 200 comprises an atraumatic tip. A rounded, atraumatic tip prevents trauma to surrounding tissues during movement of hemodialysis catheter 200, often caused from typical physiological activity, like pulsatile blood flow, catheter manipulation, or clinician manipulation. The innermost layer of organs of the vascular system is the tunica intima. If the continuous surface of the tunica intima is damaged, for example from contact by foreign devices like catheters, a thrombogenic region may form that can result in blood clotting and irregular blood flow patterns. Therefore, a atraumatic tip 215 helps prevent tissue damage.

The addition of MEMS pressure sensor 210 in hemodialysis catheter 200 can provide clinical advantages over existing catheter designs. For example, additional pressure measuring devices do not need to be introduced into the system. Additionally, MEMS pressure sensor 210 within hemodialysis catheter 200 can be used to continuously measure internal pressures such as central venous pressure (CVP) or pressure in the right atrium.

Further, pressure readings from the MEMS pressure sensor 210 can be used to determine the pressure variability index of the patient, which is the averaged beat to beat pressure variability. Moreover, dramatic changes in pressure can indicate to medical professionals that a catheter lumen has been occluded or that a fibrin sheath is forming around that catheter that is impeding blood flow. Therefore, monitoring pressure in and around hemodialysis catheters can enable early detection of either of these occlusions.

The hemodialysis catheter of the present disclosure provides additional benefits, such as providing an initial assessment of volume status, trending ability during the hemodialysis treatment, and closing pressure post-treatment. Further, when hemodialysis catheter 200 is placed in the internal jugular or subclavian position, the waveform from MEMS sensor 210 can allow for real-time guidance to enable correct positioning of hemodialysis catheter 200 in junction of the superior vena cava and right atrium or in the high right atrium.

In various embodiments, the present disclosure provides methods of performing hemodialysis comprising inserting a portion of hemodialysis catheter 200 into the vasculature of a patient. Viable insertion points include the internal jugular veins, subclavian veins, or femoral veins. In various embodiments, hemodialysis catheter 200 can be inserted using a modified Seldinger technique. In some embodiments, hemodialysis catheter 200 can be a temporary or semi-permanent, tunneled catheter. When provided as a semi-permanent, tunneled catheters, hemodialysis catheter 200 may include wide felt cuff that allows for tissue ingrowth to enable secure anchoring within the vasculature of the patient and to reduce infection.

The methods of the present disclosure further comprise zeroing the MEMS sensor and analyzing the MEMS sensor waveform to determine position of the catheter relative to the heart. Next, the methods include initiating blood flow from the patient, through the atrial lumen, to a dialyzer, through the venous lumen, and into the vasculature of the patient. Further, the methods include measuring central venous pressure and assessing volume status. Once sufficient hemodialysis is performed, the method next includes stopping the blood flow from the patient and assessing closing pressure post-treatment.

In the clinical setting, the invasive nature of hemodialysis catheters, and sensitivity of catheter-mounted sensors on other varieties of catheters, coupled with the desirability of patient mobility, makes continuous physiological monitoring difficult with existing devices. For example, some existing catheters include dedicated lumens comprising distal openings in fluid communication with transducers attached at the proximal end of the hemodialysis catheter. Because blood exhibits a tendency to coagulate during low flow and stagnant conditions, the small lumens dedicated for pressure sensing exhibit a tendency to occlude during use. Catheters of this type require periodic sensor zeroing and calibration, which can be time-consuming tasks.

For patients with precarious vascular conditions, accurate continuous or continual monitoring is beneficial for detecting irregularities and anticipating adverse events. Thus, a hemodialysis catheter with MEMS sensors provides an improvement over existing devices and can detect vascular pressures in numerous locations within the body, including the vena cava and right atrium. The accurate, real-time monitoring provided by MEMS sensors can provide rapid information on hemodynamic status.

Referring to FIG. 1, in various embodiments, exemplary monitoring system 300 may be used with hemodialysis catheter 200 to conduct continuous or continual physiologic monitoring. Monitoring system 300 may include a receiving means and a display means to collect data and display from MEMS sensors 210. In one embodiment, MEMS sensor 210 communicates with monitoring system 300 by a wired method. In another embodiment, MEMS sensor 210 communicates with monitoring system 300 wirelessly by a discreet radiofrequency. In another embodiment, MEMS sensors 210 communicates with monitoring system 300 by means of a Bluetooth radio frequency band.

As noted previously, use of MEMS sensors with the present systems can allow measurement or monitoring that is independent of patient position or movement. For example, with prior art systems that require transmission of a pressure through a lumen to a sensor, the level of the sensor with respect to the measured anatomic site can have a large influence on pressure measurements. With the present system, however, the position of monitoring system 300 with respect to the MEMS sensor 210 does not adversely affect pressure readings, and therefore, provides flexibility in terms of patient positioning and mobility.

Generally, the hemodialysis catheter of the present disclosure provides significant benefits over traditional hemodialysis catheter due to the use of accurate and durable MEMS pressure and/or temperature sensors. Additional embodiments and configurations of the present disclosure will be obvious to a person of ordinary skill in the art.

What is claimed is:

1. A method of performing hemodialysis comprising:
    inserting a portion of a hemodialysis catheter into the vasculature of a patient;
    wherein the hemodialysis catheter comprises a first tubular component and a second tubular component each extending from a proximal end to a distal end of the hemodialysis catheter, wherein the second tubular component extends a further distance at the distal end of the hemodialysis catheter than does the first tubular component, and at least one microelectricalmechanical (MEMS) sensor positioned near a distal end of the second tubular component;
    initiating blood flow from the patient, through the first tubular component to a dialyzer and from the dialyzer through the second tubular component, and into the vasculature of the patient to perform hemodialysis;
    continuously measuring internal venous blood pressure of the patient using the MEMS sensor, while performing the hemodialysis;
    assessing pressure status; and
    stopping the blood flow from the patient.

2. The method of claim 1, further comprising assessing pressure status of the patient post-treatment.

3. The method of claim 1, further comprising measuring the temperature of the patient using a temperature sensor within the hemodialysis catheter.

4. The method of claim 1, further comprising detecting catheter lumen occlusion or fibrin sheath formation from significant pressure changes.

5. The method of claim 1, further comprising advancing the distal end of the hemodialysis catheter into the right atrium of the patient and measuring the pressuring in the right atrium.

6. The method of claim 1, wherein the first tubular component and the second tubular component have an ovoid shape.

7. The method of claim 1, wherein measuring internal blood pressure comprises measuring central venous pressure.

8. The method of claim 1, wherein measuring internal blood pressure comprises measuring pressure in a right atrium of the patient.

9. The method of claim 1, wherein assessing pressure status comprises determining a pressure variability index.

* * * * *